United States Patent
Chiu et al.

(10) Patent No.: US 12,178,551 B2
(45) Date of Patent: Dec. 31, 2024

(54) HYBRID BODY TEMPERATURE MEASUREMENT SYSTEM AND METHOD THEREOF

(71) Applicant: Wistron Corporation, New Taipei (TW)

(72) Inventors: Chih-Hao Chiu, New Taipei (TW); Kuo-Hsien Lu, New Taipei (TW)

(73) Assignee: Wistron Corporation, New Taipei (TW)

( * ) Notice: Subject to any disclaimer, the term of this patent is extended or adjusted under 35 U.S.C. 154(b) by 601 days.

(21) Appl. No.: 17/348,714

(22) Filed: Jun. 15, 2021

(65) Prior Publication Data

US 2022/0330835 A1 Oct. 20, 2022

(30) Foreign Application Priority Data

Apr. 8, 2021 (TW) ................ 110112660

(51) Int. Cl.
*A61B 5/01* (2006.01)
*A61B 5/00* (2006.01)
*G06T 7/70* (2017.01)

(52) U.S. Cl.
CPC .............. *A61B 5/015* (2013.01); *A61B 5/742* (2013.01); *G06T 7/70* (2017.01); *G06T 2207/10048* (2013.01)

(58) Field of Classification Search
CPC ....... A61B 5/015; A61B 5/742; A61B 5/6844; G06T 7/70; G06T 2207/10048; G06T 2207/20021; G06T 7/77
See application file for complete search history.

(56) References Cited

U.S. PATENT DOCUMENTS

| 5,488,468 A | * | 1/1996 | Kawanishi | G01C 3/085 356/3.02 |
| 9,638,800 B1 | * | 5/2017 | Skowronek | G01S 15/42 |
| 2002/0179842 A1 | * | 12/2002 | Ookawa | H04N 5/33 348/E5.09 |

(Continued)

FOREIGN PATENT DOCUMENTS

| CN | 108615022 | | 10/2018 | |
| CN | 108615022 A | * | 10/2018 | ......... G06K 9/00342 |

(Continued)

OTHER PUBLICATIONS

English Translation of Chinese Patent Application No. CN-108615022-A (Year: 2018).*

(Continued)

*Primary Examiner* — Daniel L Cerioni
*Assistant Examiner* — Andrew E Hoffpauir
(74) *Attorney, Agent, or Firm* — JCIPRNET

(57) ABSTRACT

A hybrid body temperature measurement system and a hybrid body temperature measurement method are provided. In the method, position sensing data is obtained. The position sensing data includes an azimuth of one or more to-be-detected objects relative to a reference position. The position sensing data is mapped to a thermal image so as to generate a mapping result. The thermal image is formed in response to a temperature. A position of the to-be-detected object in the thermal image is determined according to the mapping result. Accordingly, the detection accuracy is improved.

18 Claims, 9 Drawing Sheets

(56) References Cited

U.S. PATENT DOCUMENTS

| | | | | |
|---|---|---|---|---|
| 2005/0044646 A1* | 3/2005 | Peretz | ............... | A46B 5/00 |
| | | | | 15/167.1 |
| 2009/0129655 A1* | 5/2009 | Lossev | ............... | G06T 7/0012 |
| | | | | 382/132 |
| 2017/0212739 A1* | 7/2017 | Catiller | ............... | G06F 15/7889 |
| 2017/0374296 A1* | 12/2017 | Schmidt | ............... | G01J 5/10 |
| 2018/0137631 A1* | 5/2018 | Kim | ............... | G06T 7/223 |
| 2019/0026875 A1* | 1/2019 | Yuan | ............... | G06T 5/50 |
| 2019/0333233 A1* | 10/2019 | Hu | ............... | G01S 13/04 |

FOREIGN PATENT DOCUMENTS

| | | | | |
|---|---|---|---|---|
| CN | 110579281 A | * | 12/2019 | ............... G01J 5/00 |
| CN | 111157123 | | 5/2020 | |
| TW | 202001682 | | 1/2020 | |

OTHER PUBLICATIONS

English Translation of Chinese Patent Application No. CN-110579281-A (Year: 2019).*

"Office Action of Taiwan Counterpart Application", issued on Aug. 5, 2021, p. 1-p. 8.

"Office Action of Taiwan Counterpart Application", issued on Oct. 4, 2021, p. 1-p. 8.

* cited by examiner

HYBRID BODY TEMPERATURE MEASUREMENT SYSTEM AND METHOD THEREOF

CROSS-REFERENCE TO RELATED APPLICATION

This application claims the priority benefit of Taiwan application serial no. 110112660, filed on Apr. 8, 2021. The entirety of the above-mentioned patent application is hereby incorporated by reference herein and made a part of this specification.

BACKGROUND

Technical Field

The disclosure relates to a biometric technique, and in particular, relates to a hybrid body temperature measurement system and a method thereof.

Description of Related Art

Some patients with epidemic diseases have fever or high temperature. In order to prevent these patients from entering a specific area, people passing through an entrance usually need to have their body temperature taken. It is a very convenient and safe way for control personnel to observe the body temperature of people passing by from a distance by a thermal imager. Therefore, thermal imagers are usually installed at the entrances of department stores, hospitals, mass rapid transit (MRT) stations, or other venues.

Generally, a thermal imager is set with a specific temperature threshold. When the temperature corresponding to some blocks in the thermal image exceeds this temperature threshold, the thermal imager may assume that this block has detected a human body and mark its temperature in this block. Nevertheless, the thermal imager on the market cannot identify whether this block is actually a human body or a non-biological body. For instance, the temperature of sunlight hitting the floor may exceed the temperature threshold. In addition, the thermal imagers on the market cannot identify the relative distance of the detected object. Therefore, when a human body is measured at different distances from the sensor, different temperatures may be obtained, and an error may thus be present in the detection result, and the detection result may be misjudged.

SUMMARY

Accordingly, the embodiments of the disclosure provide a hybrid body temperature measurement system and a method thereof in which a sensing result of a thermal image is combined with accurate position sensing data, and improved accuracy and identification efficiency are provided in this way.

In an embodiment of the disclosure, a hybrid body temperature measurement method is provided, and the method includes the following steps. Position sensing data is obtained. The position sensing data includes an azimuth of one or more to-be-detected objects relative to a reference position. The position sensing data is mapped to a thermal image so as to generate a mapping result. The thermal image is formed in response to a temperature. A position of one or more to-be-detected objects in the thermal image is determined according to the mapping result.

In an embodiment of the disclosure, a hybrid body temperature measurement system is provided and includes (but not limited to) a computing apparatus. The computing apparatus is configured to obtain position sensing data, mapping the position sensing data to a thermal image so as to generate a mapping result, and determining a position of one or more to-be-detected objects in the thermal image according to the mapping result. The position sensing data includes an azimuth of one or more to-be-detected objects relative to a reference position. The thermal image is formed in response to a temperature. A position of one or more to-be-detected objects in the thermal image is determined according to the mapping result.

To sum up, in the hybrid body temperature measurement system and the method thereof provided by the embodiments of the disclosure, the mapping result between the position sensing data and the thermal image is obtained, and the position of the to-be-detected object in the thermal image is accordingly determined. In this way, accuracy of body temperature measurement is improved.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

Figure 1:
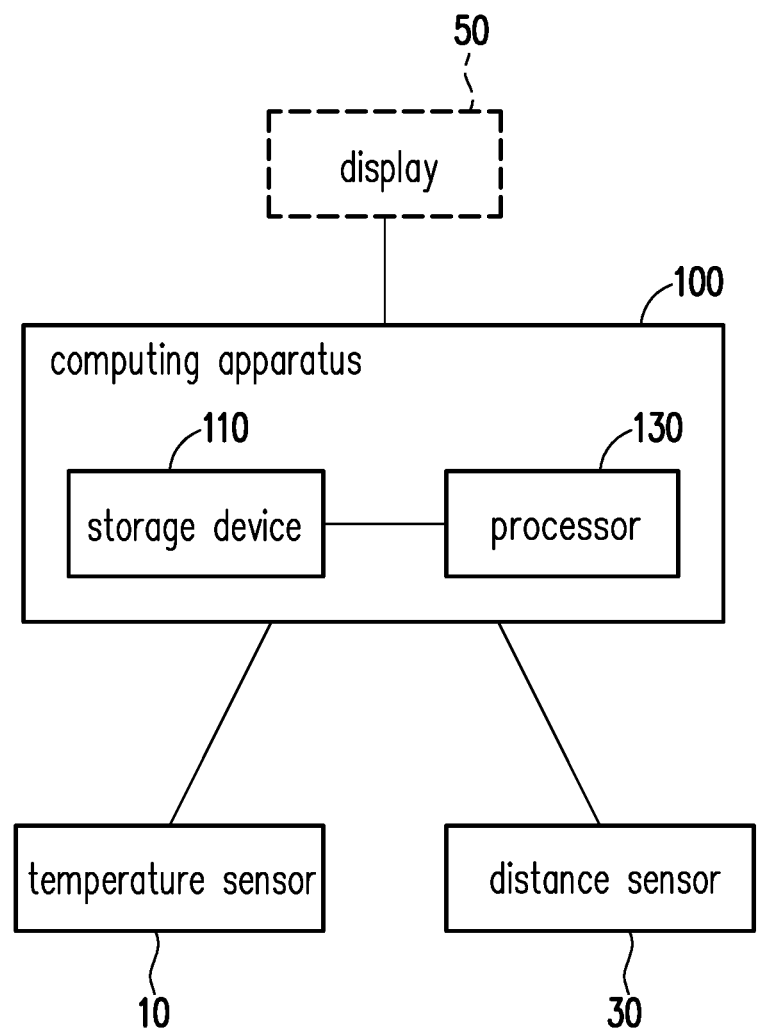
FIG. 1 is a block view of a hybrid body temperature measurement system according to an embodiment of the disclosure.

FIG. 1 is a block view of a hybrid body temperature measurement system 1 according to an embodiment of the disclosure. With reference to FIG. 1, the hybrid body temperature measurement system 1 includes (but not limited to) a temperature sensor 10, a distance sensor 30, and a computing apparatus 100.

The temperature sensor 10 may be a thermographic camera, an infrared camera, a thermal imaging camera, or other sensors that image in response to temperatures or infrared rays. The temperature sensor 10 may include, but not limited to, electronic devices such as a photosensitive device, a lens, a focusing mechanism, and an image processor that are sensitive to infrared rays. In an embodiment, the temperature sensor 10 may generate a thermal image, and sensing values (e.g., temperatures or infrared rays) on several pixels in the thermal image may form a data array (e.g., each element in the two-dimensional array corresponds to one pixel). The thermal image or the data array thereof records a temperature distribution.

The distance sensor 30 may be a radar, a time of flight (ToF) camera, a LiDAR scanner, a depth sensor, an infrared rangefinder, an ultrasonic sensor, or other range-related sensors. In an embodiment, the distance sensor 30 may detect an azimuth of a to-be-detected object, that is, the azimuth of the to-be-detected object relative to the distance sensor 30. In another embodiment, the distance sensor 30 may detect a distance of the to-be-detected object, that is, the distance between the to-be-detected object and the distance sensor 30. In still another embodiment, the distance sensor 30 may detect a number of the to-be-detected object in a field of view (FOV). In some embodiments, one or more detection results (e.g., the azimuth, distance, and/or number) described above may act as position sensing data.

In an embodiment, both the distance sensor 30 and the temperature sensor 10 are disposed in a vertical direction of a specific reference position. This reference position may be determined according to actual needs of a user. For instance, this reference position is in the middle of a desktop.

The computing apparatus 100 may be a desktop computer, a notebook computer, a smartphone, a tablet computer, a server, a thermal imager, or other computing apparatuses. The computing apparatus 100 includes (but not limited to) a storage device 110 and a processor 130. The computing apparatus 100 is coupled to the distance sensor 30 and the temperature sensor 10.

The storage device 110 may be a fixed or movable random-access memory (RAM) in any form, a read only memory (ROM), a flash memory, a hard disk drive (HDD), a solid-state drive (SSD), or other similar devices. In an embodiment, the storage device 110 is configured to record program codes, software modules, configurations, data (e.g., thermal images, position sensing data, temperature, position, decision results, etc.), or files, and description thereof is provided in detail in following embodiments.

The processor 130 is coupled to the storage device 110, and the processor 130 may be a central processing unit (CPU), a graphic processing unit (GPU), or other programmable microprocessors for general or special use, a digital signal processor (DSP), a programmable controller, a field programmable gate array (FPGA), an application-specific integrated circuit (ASIC), a neural network accelerator, other similar devices, or a combination of the foregoing devices. In an embodiment, the processor 130 is configured to execute all or part of the operations of the computing apparatus and may load and execute the program codes, software modules, files, and data recorded by the storage device 110.

In some embodiments, the hybrid body temperature measurement system 1 further comprises a display 50. The display 50 may be a liquid-crystal display (LCD), a light-emitting diode (LED) display, an organic light-emitting diode (OLED) display, a quantum dot display, or other types of displays. The display 50 is coupled to the computing apparatus 100. In an embodiment, the display 50 is configured to display a thermal image.

In an embodiment, the apparatuses and/or devices in the hybrid body temperature measurement system 1 may be integrated into an independent apparatus. In another embodiment, part of the apparatuses and/or devices in the hybrid body temperature measurement system 1 may be integrated into an independent apparatus and may communicate with other apparatuses and/or devices to obtain data. For instance, the thermal imager (including the computing apparatus 100, the temperature sensor 10, and the display 50) is externally connected to the distance sensor 30 or is directly integrated with the distance sensor 30.

In the following paragraphs, a method provided by the embodiments of the disclosure is described together with the various apparatuses, devices, and modules in the hybrid body temperature measurement system 1. The steps of the method may be adjusted according to actual implementation and are not particularly limited.

Figure 2:
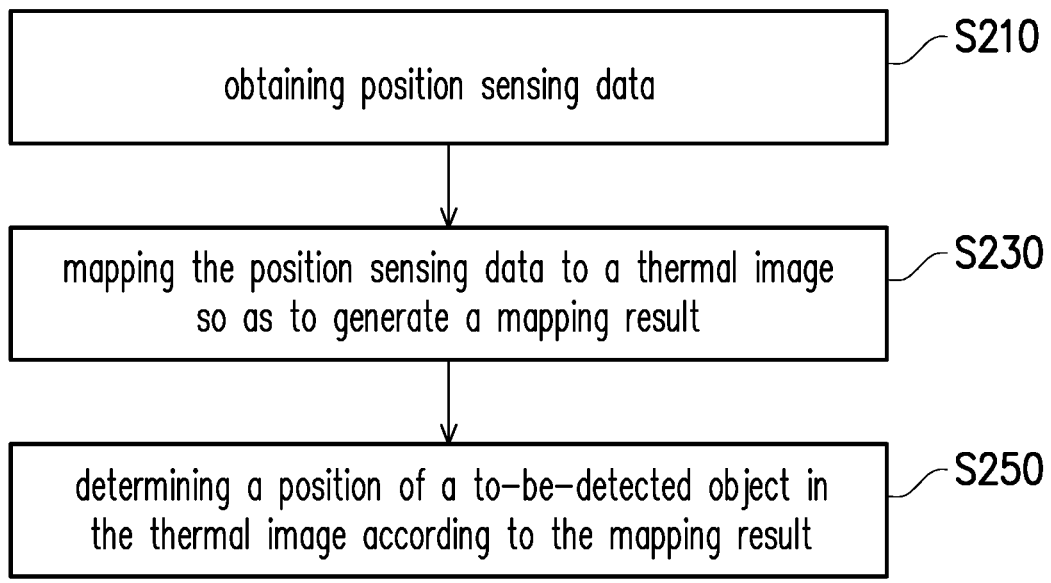
FIG. 2 is a flow chart of a hybrid body temperature measurement method according to an embodiment of the disclosure.

FIG. 2 is a flow chart of a hybrid body temperature measurement method according to an embodiment of the disclosure. With reference to FIG. 2, the processor 130 may obtain the position sensing data (step S210). To be specific, the distance sensor 30 may generate the position sensing data. In an embodiment, the position sensing data includes the azimuth of the to-be-detected object relative to the reference position. The to-be-detected object is, for example, a person, a cat, a dog, or other biological bodies, or the ground, a table, a chair, or other non-biological bodies. The reference position is the position where the temperature sensor 10 and the distance sensor 30 is located. In another embodiment, the position sensing data includes a distance between the to-be-detected object and the reference position. In another embodiment, the position sensing data includes a number of the to-be-detected object.

The processor 130 may map the position sensing data to a thermal image so as to generate a mapping result (step S230). To be specific, the temperature sensor 10 may generate the thermal image. Note that in the related art, the position sensing data may not be directly converted into a coordinate point or a position on the thermal image. In the embodiments of the disclosure, the position sensing data and the thermal image are combined to obtain an accurate final identification result (related to the number, position, and/or distance) of the to-be-detected object). It thus can be seen that in the embodiments of the disclosure, a relationship (corresponding to the mapping result) between the position sensing data and the thermal image is required to be obtained.

Figure 3:
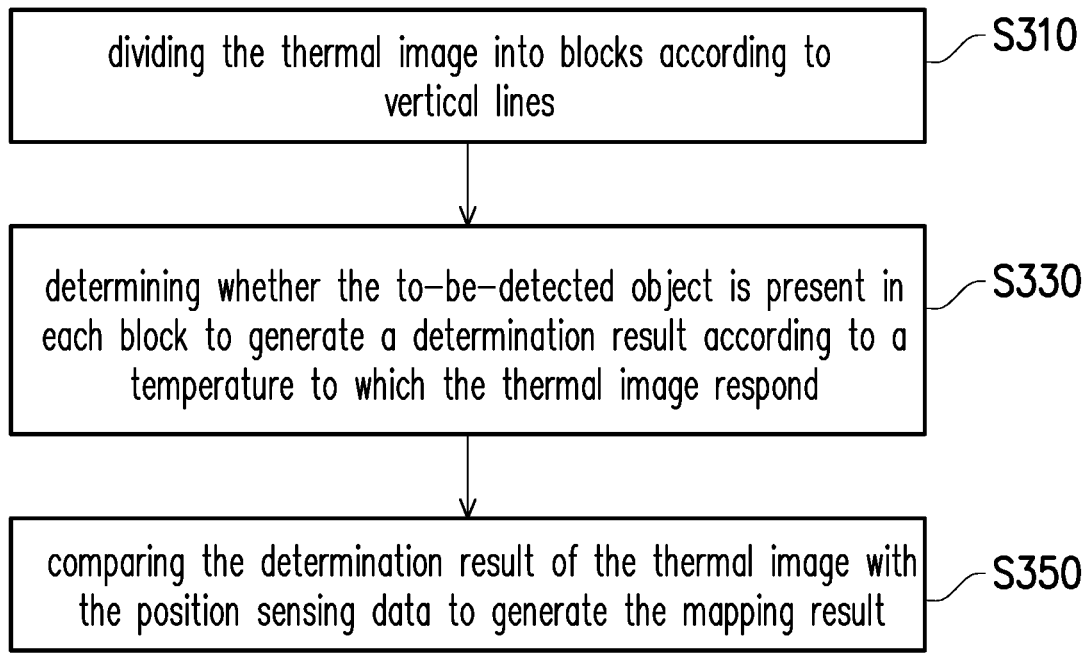
FIG. 3 is a flow chart of generation of a mapping result according to an embodiment of the disclosure.

FIG. 3 is a flow chart of generation of a mapping result according to an embodiment of the disclosure. With reference to FIG. 3, in an embodiment, the processor 130 may divide the thermal image into a plurality of blocks according to a plurality of vertical lines (step S310). To be specific, in the following paragraphs, a left-right direction of the thermal image is regarded as a horizontal direction (or a transverse direction), and an up-down direction of the thermal image is regarded as a vertical direction (or a longitudinal direction). Note that the temperature sensor 10 has a specific FOV. Content in the thermal image is the object and/or scene covered by this FOV. It thus can be seen that if two to-be-detected objects are located at different positions in the horizontal direction in the thermal image, it represents different azimuths of the two to-be-detected objects relative to the reference position (i.e., the position where the temperature sensor 10 is located). Division of the thermal image in the vertical direction id to obtain the azimuth of the to-be-detected object relative to the reference position.

Figure 4:
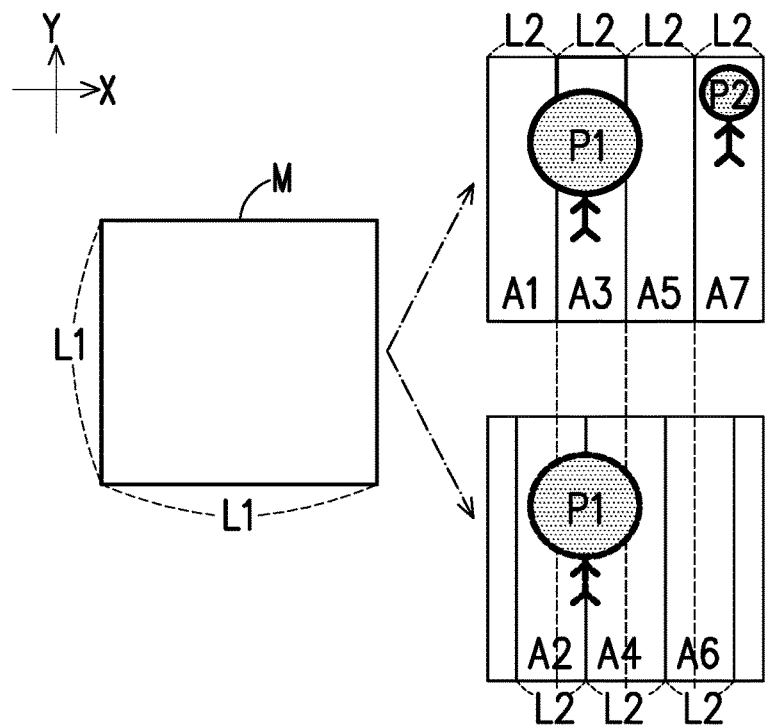
FIG. 4 is a schematic diagram of division of blocks according to an embodiment of the disclosure.

For instance, FIG. 4 is a schematic diagram of division of blocks A1 to A7 according to an embodiment of the disclosure. With reference to FIG. 4, assuming that a thermal image M is L1*L1 (e.g., a length L1 is 80 pixels), an X axis is the horizontal direction, and a Y axis is the vertical direction. Blocks A1, A3, A5, and A7 are divided by the processor 130 every other length L2 (e.g., 20 pixels). Herein, a person P1 and a person P2 (i.e., the to-be-detected objects) are located in different blocks. Besides, blocks A2, A4, and A6 may be further divided every other length L2 after the processor 130 is shifted by a specific length (e.g., 10 pixels) on the leftmost side. Herein, the blocks A1 and A3 and the block A2 are partially overlapped, and overlapping of the rest of the blocks may be deduced by analogy. It thus can be seen that in a scene where multiple people are present at the same time, these people are present in a single block or multiple blocks of the thermal image M. As shown in FIG. 3, the person P1 covers the blocks A1 to A5, and the person P2 covers the blocks A6 to A7.

Note that the lengths, shapes, numbers, and division manners are only used as examples for illustration and are not intended to limit the disclosure, and a user may change the numerical values or content according to actual needs. For instance, the number of blocks may be increased or decreased in response to sensitivity of actual applications.

Figure 5:
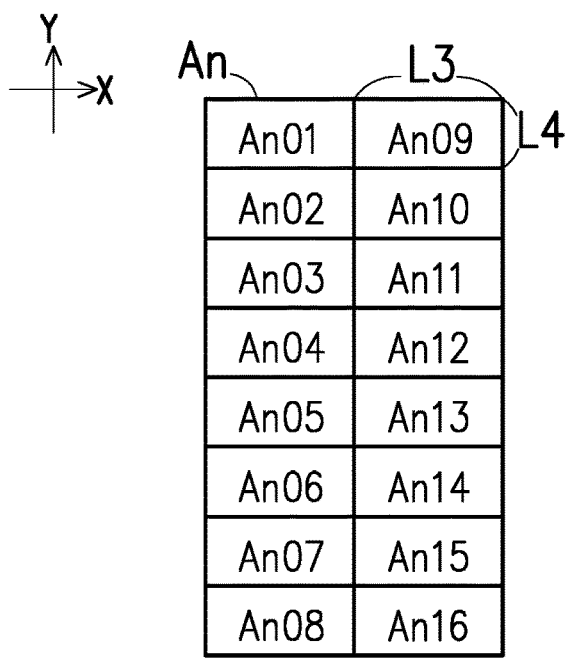
FIG. 5 is a schematic diagram of division of sub-blocks according to an embodiment of the disclosure.

In order to further confirm whether the to-be-detected object is present on a block in the thermal image, the processor 130 may divide one or more blocks into one or more sub-blocks. For instance, FIG. 5 is a schematic diagram of division of sub-blocks An01 to An16 according to an embodiment of the disclosure. With reference to FIG. 5, the processor 130 further may divide a block An (n is a positive integer, and An is, for example, one of the blocks A1 to A7 in FIG. 4) into a plurality of sub-blocks An01 to An16 each with a size of L3*L4 (e.g., each of the lengths L3 and L4 is 10 pixels).

Note that as shown in FIG. 5, the block An is divided with equal length in the vertical direction and the horizontal direction. Nevertheless, in other embodiments, the number of the blocks to be divided and the dividing direction may be changed according to application needs.

With reference to FIG. 3, the processor 130 may determine whether the to-be-detected object is present in each of the blocks to generate a determination result according to a temperature to which the thermal image respond (step S330). To be specific, after the thermal image is divided into multiple blocks and multiple sub-blocks, the processor 130 may confirm that the designated to-be-detected object is present in which of those blocks and/or sub-blocks or confirm that the to-be-detected object enters or exits this block and/or sub-block.

In an embodiment, the processor 130 may determine a representative temperature of one or multiple sub-blocks in each of the blocks and determine whether one or more to-be-detected objects are present in the corresponding block according to a comparison result of the representative temperature and a temperature threshold. This representative temperature may be related to a standard deviation, a mean, or a mode. The comparison result may be equal, greater than, less than, not greater than, or not less than.

Figure 6:
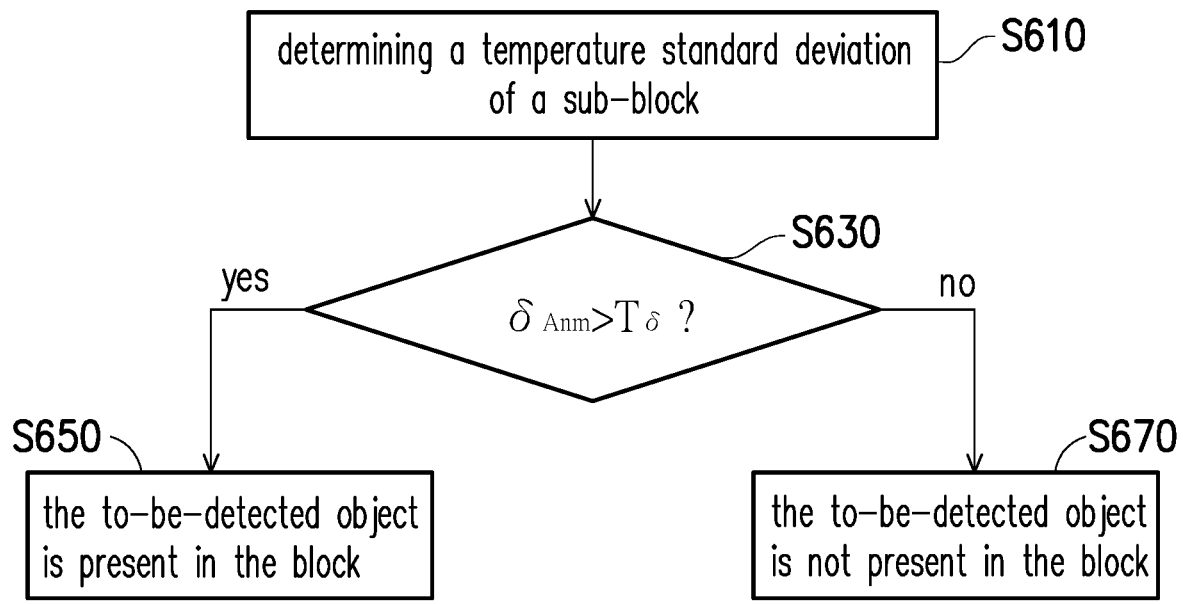
FIG. 6 is a flow chart of a first temperature determination condition according to an embodiment of the disclosure.

FIG. 6 is a flow chart of a first temperature determination condition according to an embodiment of the disclosure. With reference to FIG. 6, the processor 130 may determine an average temperature of each sub-block and determine a temperature standard deviation of these average temperatures calculated in the sub-blocks in a specific time interval (e.g., 500 or 1,000 milliseconds, related to sensitivity of actual applications) (step S610). The processor 130 may determine whether a temperature standard deviation $\delta_{Anm}$ of each sub-block Anm (m is a positive integer, e.g., one of 1 to 16 in FIG. 5) in the block An is greater than a standard deviation threshold $T_\delta$ (depending on empirical values applied in different fields) (step S630). Herein, the representative temperature is the temperature standard deviation $\delta_{Anm}$, and the temperature threshold is the standard deviation threshold $T_\delta$. If the temperature standard deviation $\delta_{Anm}$ of any one or more sub-blocks Anm is determined to be greater than the standard deviation threshold $T_\delta$ (i.e., the comparison result), the processor 130 may determine that the to-be-detected object is present in or enters and exits this block An to which the processor 130 belongs (i.e., the determination result) (step S650). If the temperature standard deviation $\delta_{Anm}$ of all or a specific number of the sub-blocks Anm is determined not to be greater than the standard deviation threshold $T_\delta$ (i.e., the comparison result), the processor 130 may determine that the to-be-detected object is not present in or does not enter and exit this block An to which the processor 130 belongs (i.e., the determination result) (step S670).

For instance, in an indoor environment where there is no strong wind, a change of data within 1,000 milliseconds is observed. That is, the standard deviation threshold $T_\delta$ is 0.1, and the time interval is 1,000 milliseconds. If the data does not change considerably during this 1 second, the temperature standard deviation $\delta_{Anm}$ may approach 0 and be less than the standard deviation threshold $T_\delta$, indicating that no objects enter or exit a range of this block An. In contrast, it means that the to-be-detected object enters and exits this block An.

The first temperature determination condition mainly relies on the overall momentum to observe whether the to-be-detected object enters the range of the block, but it may not be determined whether the object is a biological body or thermal disturbance. Therefore, a second temperature determination condition is further provided by the embodiments of the disclosure.

Figure 7:
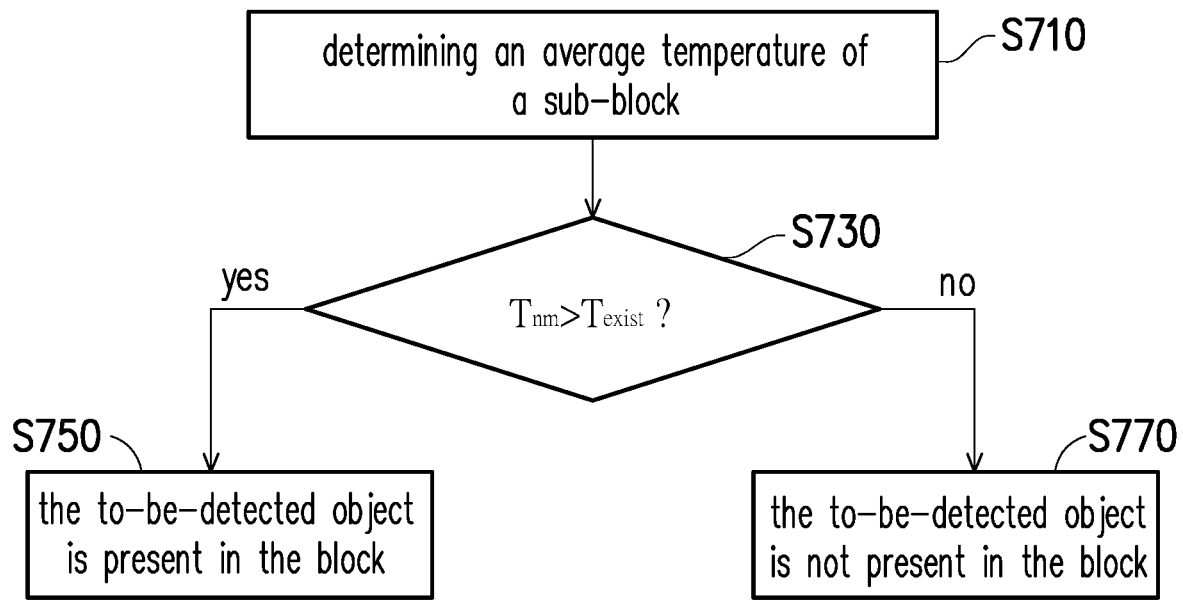
FIG. 7 is a flow chart of a second temperature determination condition according to an embodiment of the disclosure.

FIG. 7 is a flow chart of the second temperature determination condition according to an embodiment of the disclosure. With reference to FIG. 7, the processor 130 may determine an average temperature of each of the sub-blocks (step S710). The processor 130 may determine whether an average temperature $T_{nm}$ of each sub-block Anm in the block An is greater than an average threshold $T_{exist}$ (step S730). Herein, the representative temperature is the average temperature $T_{nm}$, and the temperature threshold is the average threshold $T_{exist}$ (the value is usually a lower limit value of the body temperature of a to-be-detected object of a specified type, for example, the human body is 34 to 35 degrees). If the average temperature $T_{nm}$ of any one or more sub-blocks Anm is determined to be greater than the average threshold $T_{exist}$ (i.e., the comparison result), the processor 130 may determine that the to-be-detected object is present in or enters and exits this block An to which the processor 130 belongs (i.e., the determination result) (step S750). If the average temperature $T_{nm}$ of all of or a specific number of the sub-blocks Anm is determined not to be greater than the average threshold $T_{exist}$ (i.e., the comparison result), the processor 130 may determine that the to-be-detected object is not present in or does not enter and exit this block An to which the processor 130 belongs (i.e., the determination result) (step S770).

With reference to FIG. 3, the processor 130 may compare the determination result of the thermal image with the position sensing data to generate the mapping result (step S350). To be specific, the processor 130 finds correlation between the determination result of the thermal image and the position sensing data. This correlation includes a corresponding relationship of the azimuth.

Figure 8:
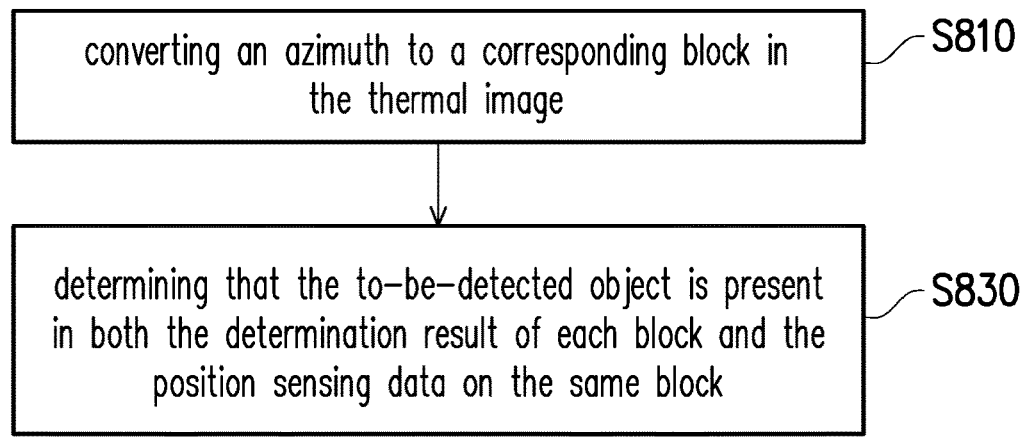
FIG. 8 is a flow chart of comparison of data according to an embodiment of the disclosure.

FIG. 8 is a flow chart of comparison of data according to an embodiment of the disclosure. With reference to FIG. 8, the processor 130 may convert the azimuth corresponding to one or more to-be-detected objects into the position sensing data to a corresponding block in the thermal image (step S810). To be specific, since different blocks correspond to different azimuths, the processor 130 may correspond the azimuth of the position sensing data to a specific block. In the planning of the apparatus, a user may set center positions of the distance sensor 30 and the temperature sensor 10 to be overlapped in the up-down/vertical direction, such that center points of a horizontal viewing angle of the distance sensor 30 and a horizontal viewing angle of the temperature sensor 10 are matched at a position where the X axis is the horizontal center.

Figure 9:
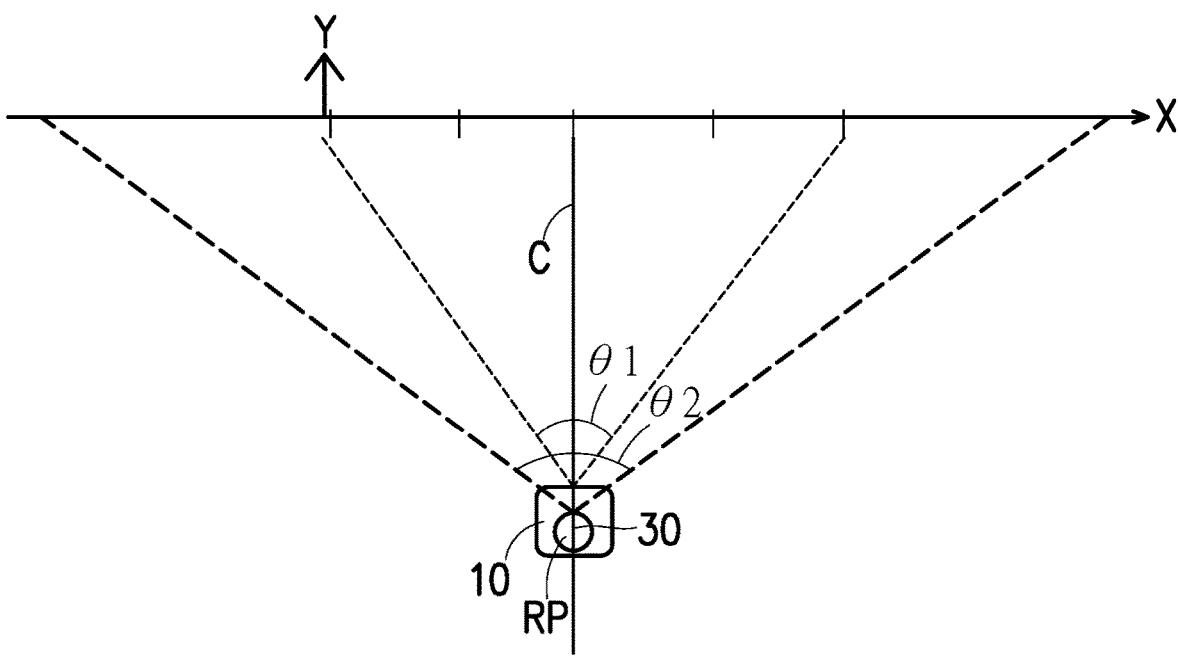
FIG. 9 is a schematic diagram of conversion of an azimuth according to an embodiment of the disclosure.

For instance, FIG. 9 is a schematic diagram of conversion of an azimuth according to an embodiment of the disclosure. With reference to FIG. 9, the temperature sensor 10 and the distance sensor 30 are both located on a reference position RP. Assuming that the size of the thermal image is 80*80, an X-axis coordinate covered by a viewing angle θ1 of the temperature sensor 10 is 0 to 80, and an X-axis coordinate of a horizontal center C is 40. Besides, the distance sensor 30 has the same horizontal center C under a viewing angle θ2.

Besides, a formula for azimuth conversion is provided as follows:

$$T_{angle} = R_{angle} - (RA_{max} - TA_{max})/2 \quad (1)$$

where $RA_{max}$ is the maximum horizontal viewing angle θ2 (corresponding to FOV thereof) of the distance sensor 30, $TA_{max}$ is the maximum horizontal viewing angle θ1 (corresponding to FOV thereof) of the temperature sensor 10, $R_{angle}$ is the azimuth of the position sensing data before the conversion, and $T_{angle}$ is the azimuth of the position sensing data after the conversion.

The converted X axis coordinate is:

$$T_{xpos} = T_{angle} * (TX_{max}/TA_{max}) \quad (2)$$

where $TX_{max}$ is the size/length (e.g., 80 in FIG. 4 or FIG. 9) of the thermal image in the horizontal direction, and $T_{xpos}$ is the X axis coordinate after the conversion. That is, the converted coordinates are obtained based on a proportional relationship between the angle and the length.

If it is intended to confirm the block to which the azimuth of the position sensing data belongs (that is, which of the blocks An is the X-axis coordinate $T_{xpos}$ located), the processor 130 may determine an X-axis coordinate $V_n$, which is perpendicular to a central line/bisector of the X axis, of the block An closest to the X-axis coordinate $T_{xpos}$.

$$|T_{xpos} - V_n| < (I_{AN}/2) \quad (3)$$

where $I_{AN}$ is a gap between central lines of adjacent blocks (taking block division in FIG. 4 as an example, $I_{AN} = TX_{max}/8$). If formula (3) is satisfied, the processor 130 then determines that the X axis coordinate $T_{xpos}$ is located in this block An, and on the contrary, the processor 130 determines that the X axis coordinate $T_{xpos}$ is not located in this block An.

Note that the proportional relationship between the formulas (1) and (2) is based on the assumption that the viewing angle θ2 is different from the viewing angle θ1. Nevertheless, in other embodiments, if the viewing angle θ2 is equal to the viewing angle θ1, the formulas (1) and (2) may be ignored.

The processor 130 may determine that one or more to-be-detected objects are present in both the determination result of each of the blocks and the position sensing data on the same block and accordingly generates the mapping result. To be specific, if the azimuth of the position sensing data is mapped to a specific block in the thermal image, the processor 130 may then further compare two pieces of data (i.e., the position sensing data and the thermal image) on the same block.

In an embodiment, the processor 130 may determine whether the to-be-detected object (assumed to be a biological body, such as a human body) is present in each of the blocks according to a determination table. A determination table described in an embodiment is shown in Table (1):

TABLE 1

| Situation | Result of Formula (3) | Result of First Temperature Determination Condition | Result of Second Temperature Determination Condition | Determination Result: Presence of To-Be-Detected Object | Description |
| --- | --- | --- | --- | --- | --- |
| 1 | yes | yes | yes | yes | moving to-be-detected object detected |
| 2 | yes | yes | no | no | floating non-biological body obstacle detected |
| 3 | yes | no | yes | yes | static to-be-detected object detected |
| 4 | yes | no | no | no | fixed non-biological body obstacle detected |
| 5 | no | yes | yes | yes | thermal disturbance or |

TABLE 1-continued

| Situation | Result of Formula (3) | Result of First Temperature Determination Condition | Result of Second Temperature Determination Condition | Determination Result: Presence of To-Be-Detected Object | Description |
|---|---|---|---|---|---|
| 6 | no | yes | no | no | edge of to-be-detected object detected environmental change detected |
| 7 | no | no | yes | no | interference source of thermal object or edge of to-be-detected object present in environment |
| 8 | no | no | no | no | no object detected | where the "yes" in the Result of Formula (3) means that the to-be-detected object is detected in the position sensing data regarding the azimuth corresponding to this block. The "yes" in the Result of First Temperature Determination Condition means that the temperature variation of this block is significant, and the "yes" in the Result of Second Temperature Determination Condition means that a to-be-detected object of a specific type is detected in this block, and vice versa. The rest may be deduced by analogy, and description thereof is not repeated herein.

In an embodiment, the processor 130 may determine that the to-be-detected object is present in both the determination result of each of the blocks and the position sensing data on the same block (step S830) and accordingly generates the mapping result. The mapping result includes that one or more to-be-detected objects are present in at least one of the blocks. Taking Table (1) as an example, the determination result of Situation 1 and Situation 3 is that the to-be-detected object is detected ("yes"). Herein, in the case that the temperature variation is not excessively significant (the Result of First Temperature Determination Condition is "no"), the determination result is related to a static to-be-detected object. In the case that the temperature variation is excessively significant (the Result of First Temperature Determination Condition is "yes"), the determination result is related to a moving to-be-detected object.

In another embodiment, the mapping result may also be that the to-be-detected object is not detected in the block. For instance, in Table (1), except for Situation 1 and Situation 3, all other situations are regarded as not detecting the to-be-detected object.

With reference to FIG. 2, the processor 130 may determine a position of the to-be-detected object in the thermal image according to the mapping result (step S250). To be specific, the mapping result may be configured to assist in confirming the actual position of the to-be-detected object in the thermal image. This position is, for example, the coordinates of the to-be-detected object in a two-dimensional coordinate system formed by the thermal image. This position may also be a relative position of the to-be-detected object and other reference points in the thermal image.

Figure 10:
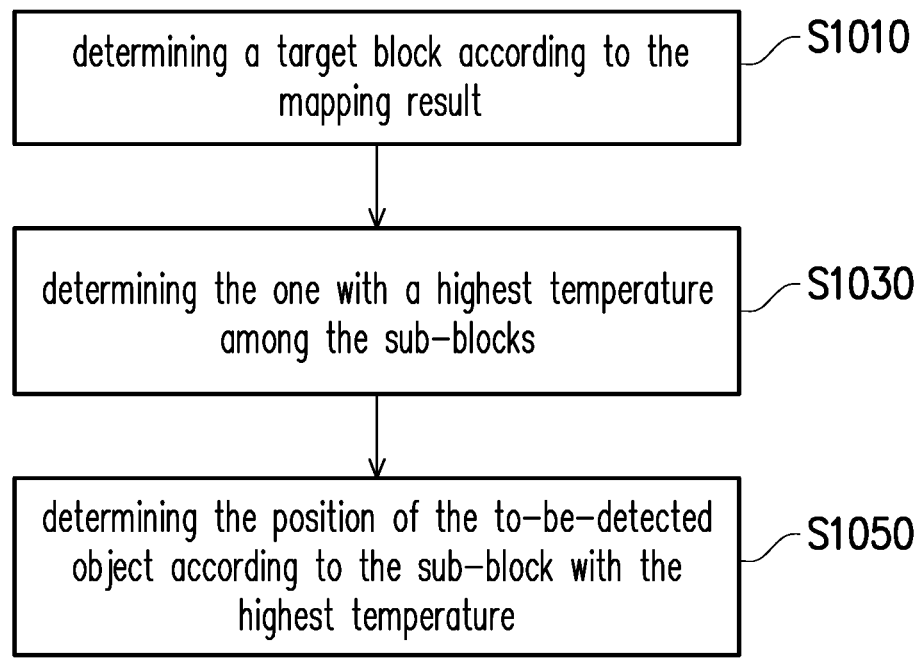
FIG. 10 is a flow chart of determination of a position according to an embodiment of the disclosure.

FIG. 10 is a flow chart of determination of a position according to an embodiment of the disclosure. With reference to FIG. 10, the processor 130 may determine a target block according to the mapping result (S1010). Herein, the target block is the block where the to-be-detected object is confirmed to be present after comparison of two pieces of data. For example, the block satisfying both Situation 1 and Situation 3 in Table (1) is the target block. For another example, the block satisfying only Situation 1 in Table (1) is the target block. For still another example, the block satisfying only Situation 3 in Table (1) is the target block.

The processor 130 may determine the one with a highest temperature among the plurality of sub-blocks in each target block in the thermal image (step S1030). To be specific, the processor 130 may select one or more sub-blocks with the highest temperature according to the Result of Second Temperature Determination Condition (e.g., the average temperature is greater than the average threshold). Herein, determination of the highest temperature may be made based on the numerical value or an upper limit value of the comparison.

The processor 130 may determine the position of the to-be-detected object according to the sub-block with the highest temperature (step S1050). For instance, the processor 130 treats the coordinates of the center point, the upper right corner, or any position within the range of the sub-block as the position of the to-be-detected object.

Figure 11:
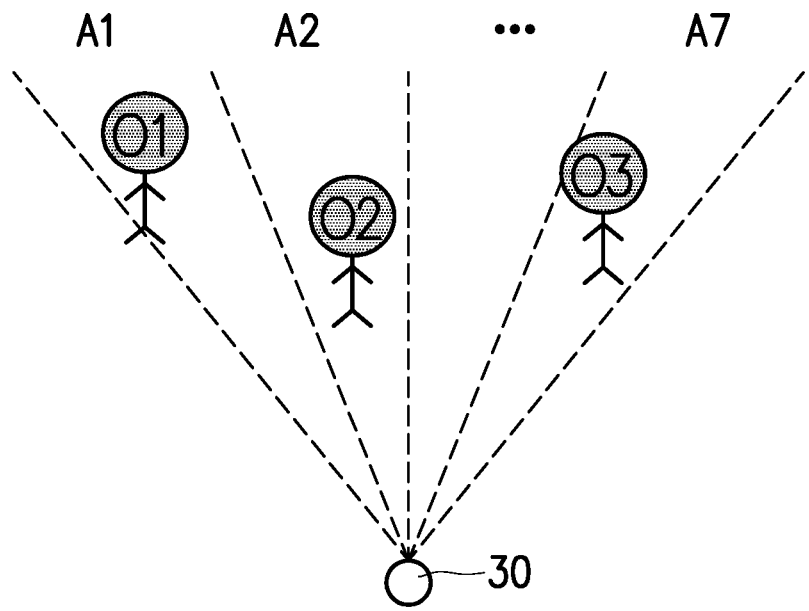
FIG. 11 is a schematic diagram of the mapping result according to an embodiment of the disclosure.

In an embodiment, regarding relative distances of the to-be-detected object recorded in the position sensing data, the processor 130 may map these distances to the blocks in the thermal image. To be specific, FIG. 11 is a schematic diagram of the mapping result according to an embodiment of the disclosure. With reference to FIG. 11, assuming that to-be-detected objects O1 to O3 are respectively located in blocks A1, A2, and A7. The mapping result may be found with reference to Table (2):

TABLE 2

| Object Detected | Distance (cm) | Block Converted from Azimuth of Position Sensing Data |
|---|---|---|
| to-be-detected object O1 | 80 | A1 |
| to-be-detected object O2 | 63 | A2 |
| to-be-detected object O3 | 70 | A7 |

Figure 12:
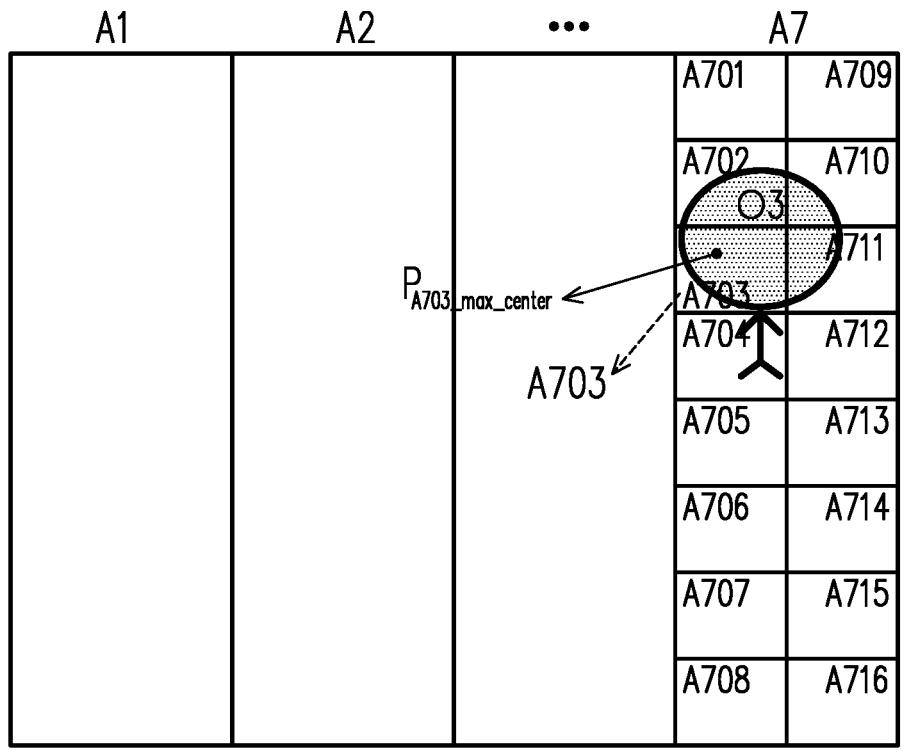
FIG. 12 is a schematic diagram of determination of a position according to an embodiment of the disclosure.

In addition, regarding a position of the to-be-detected object O3, FIG. 12 is a schematic diagram of determination of a position according to an embodiment of the disclosure. With reference to FIG. 12, the to-be-detected object O3 is located in the block A7. Assuming that sub-blocks A702, S703, A710, and A711 satisfy the second temperature determination condition (i.e., the average temperature is greater than the average threshold). If the sub-block with the highest temperature among these sub-blocks A702, S703, A710, and A711 is the sub-block A703, the processor 130 may define that the center point of this sub-block A703 is a position $P_{A703\_max\_center}$ where the to-be-detected object O3 is located.

Figure 13:
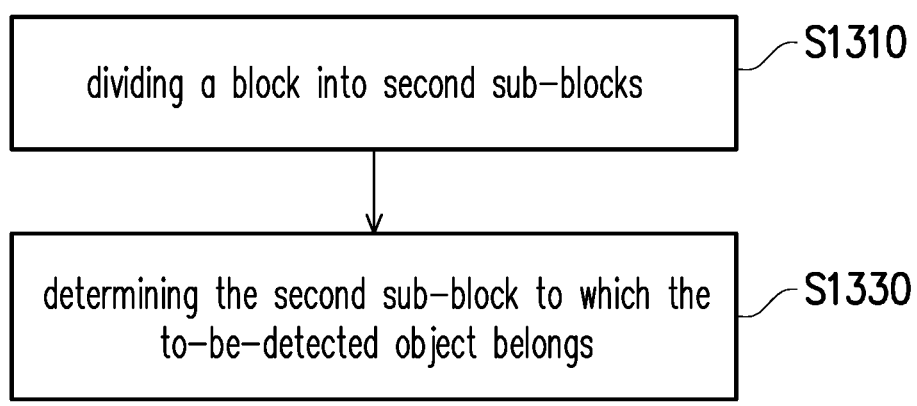
FIG. 13 is a flow chart of determination of positions of multiple people according to an embodiment of the disclosure.

Regarding determination of positions of multiple people, FIG. 13 is a flow chart of determination of positions of multiple people according to an embodiment of the disclosure. With reference to FIG. 13, the processor 130 may divide the target block into a plurality of second sub-blocks according to a number of the distances corresponding to the target block (step S1310). Herein, the mapping result includes a plurality of the distances corresponding to one specific target block. That is, a plurality of to-be-detected objects are detected in the range (corresponding to this target block) of a specific azimuth of the position sensing data, or the detected number is greater than one.

Figure 14:
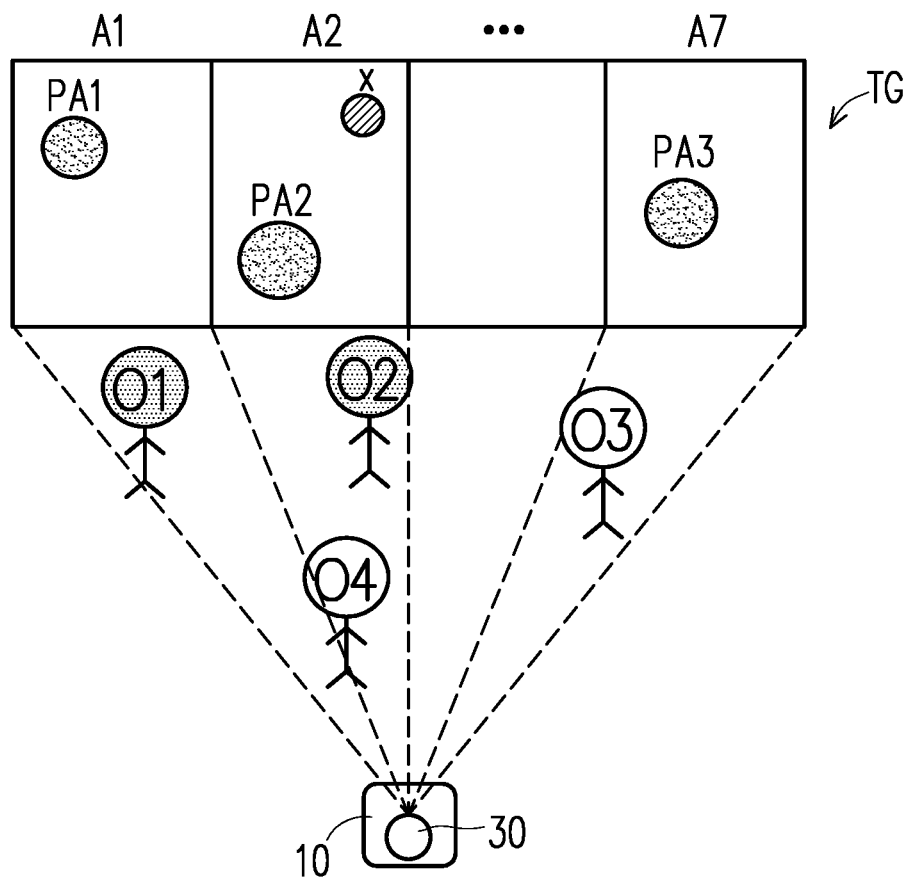
FIG. 14 to FIG. 16 are schematic diagrams of determination of the positions of multiple people according to an embodiment of the disclosure.

For instance, FIG. 14 is a schematic diagram of determination of the positions of multiple people according to an embodiment of the disclosure, and Table (3) is the mapping result. With reference to FIG. 14 and Table (3), in a thermal image TG, a position PA1 of the to-be-detected object O1 and a position PA3 of the to-be-detected object O3 may both be determined. Nevertheless, the block A2 corresponds to two distances. Therefore, it is not yet possible to determine to which that the position PA2 of the one with the highest temperature corresponds.

TABLE 3

| Object Detected | Distance (cm) | Block Converted from Azimuth of Position Sensing Data |
| --- | --- | --- |
| to-be-detected object O1 | 80 | A1 |
| to-be-detected object O2 | 100 | A2 |
| to-be-detected object O3 | 70 | A7 |
| to-be-detected object O4 | 50 | A2 |

Figure 15:
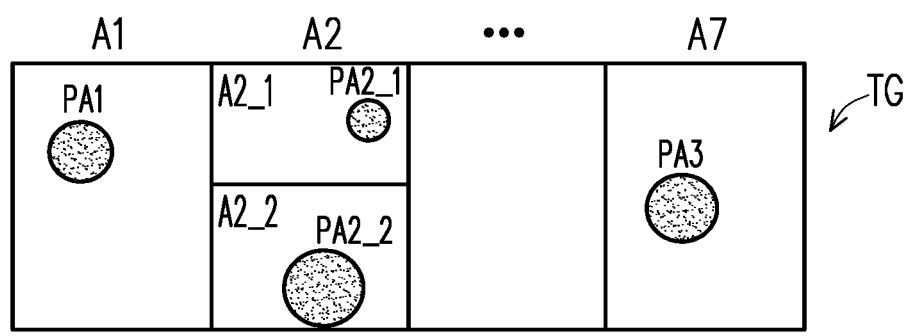

FIG. 15 is a schematic diagram of determination of the positions of multiple people according to an embodiment of the disclosure. With reference to FIG. 15, the processor 130 may divide the block A2 by the number (e.g., two) recorded in the position sensing data of the block A2 into the same number of second sub-blocks A2_1 and A2_2. Note that the number and sizes of the second sub-blocks are determined according to actual needs.

With reference to FIG. 13, the processor 130 may determine the second sub-block corresponding to the to-be-detected object. The to-be-detected object corresponds to the distances, and the distances correspond to the target block. In the thermal image, if the distance from the distance sensor 30 is farther, its position may be closer to the second block at the top of the screen, and in contrast, the closer the distance is, the position may be closer to the bottom of the screen. In addition, similarly, according to steps S1030 and S1050, the processor 130 may determine the position of the one with the highest temperature in the second sub-block, that is, a representative position of the highest one among the sub-blocks whose average temperatures in the second sub-blocks are greater than the average threshold.

Figure 16:
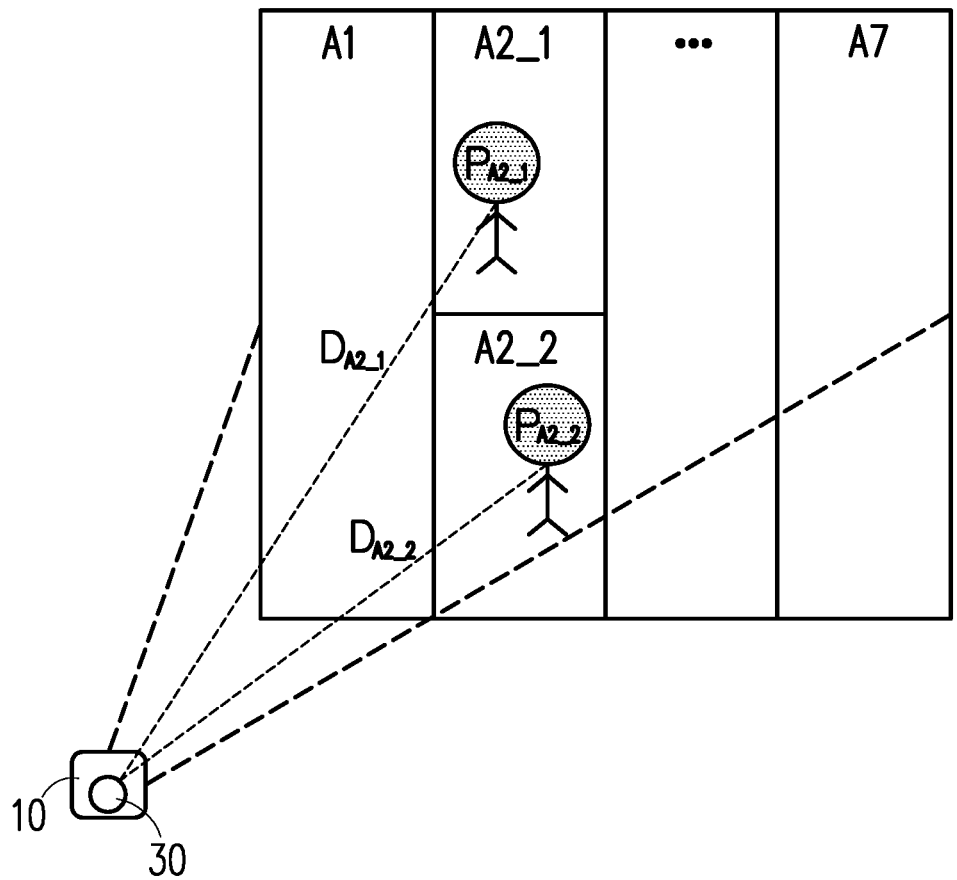

FIG. 16 is a schematic diagram of determination of the positions of multiple people according to an embodiment of the disclosure. With reference to FIG. 14 to FIG. 16 and Table (3), a distance $D_{A2\_1}$ of the to-be-detected object O2 is 100 cm, so it belongs to the second block A2_1 (the distance is farther, the second sub-block is higher), and its position is $P_{A2\_1}$. A distance $D_{A2\_2}$ of the to-be-detected object O4 is 50 cm, so it belongs to the second block A2_2 (the distance is farther, the second sub-block is lower), and its position is $P_{A2\_2}$. Therefore, the mapping result may be updated as shown in Table (4) as follows:

TABLE 4

| Object Detected | Distance (cm) | Block Converted from Azimuth of Position Sensing Data |
| --- | --- | --- |
| to-be-detected object O1 | 80 | A1 |
| to-be-detected object O2 | 100 | A2_1 |
| to-be-detected object O3 | 70 | A7 |
| to-be-detected object O4 | 50 | A2_2 |

If only the thermal image is analyzed, the distance of the to-be-detected object may not be clearly known, and the number of people may not be identified. Nevertheless, in the embodiments of the disclosure, the position sensing data of the distance sensor 30 is combined, so that the distance may be further confirmed, and multiple to-be-detected objects may be identified.

In order to obtain an accurate temperature sensing value, in an embodiment, the processor 130 may compensate a temperature corresponding to the to-be-detected object in the thermal image according to the position of the one to-be-detected object in the thermal image. The processor 130 may provide corresponding temperature correction tables for different distances. The common temperature correction method used by the temperature measurement apparatuses on the market (e.g., forehead thermometers, etc.) is linear correction. That is, a temperature-stabilized heat source apparatus (e.g., a blackbody furnace, which can produce a specified uniform temperature on the surface of a machine) is set up, and the temperature-stabilized heat source apparatus is adjusted to a fixed temperature point. An operator then uses a temperature measurement apparatus to measure the temperature-stabilized heat source apparatus to obtain the temperature value. Next, the above actions are repeated, and the temperature-stabilized heat source apparatus is adjusted to several different temperature points, e.g., 33, 35, 36, 37, and 38 degrees. The temperature measured by the temperature measurement apparatus may be recorded as a reference temperature data set. On the other hand, the temperature sensor 10 may also measure the temperature-stabilized heat source apparatus at different temperatures at the same time and performs recording as the to-be-corrected temperature data set. In addition, the operator may change the distance between the temperature sensor 10 and the temperature-stabilized heat source apparatus and measures the temperature-stabilized heat source apparatus at different temperatures.

In applications, the temperature sensor 10 is used to measure the to-be-detected object. If a value x is obtained, the processor 130 needs to determine a position in which a temperature interval I of the value x may fall in the to-be-corrected temperature data set. Next, the processor 130 finds a linear slope value a and an offset value b of the temperature interval I in a reference temperature data set to compensate the value x and outputs a corrected temperature y, which is the accurate body temperature.

$$y = ax + b \quad (4)$$

Formula (4) (static correction formula) is applied to the aforementioned body temperature measurement results of one person or multiple people, and the processor 130 may correct the temperatures of different to-be-detected objects. Inevitably, the to-be-detected object may move in real applications. If the measurement result of the temperature sensor 10 is compared with the result of the temperature measurement apparatus (e.g., a forehead thermometer) as a reference, the temperature value obtained by formula (4) may be slightly lower. During the correction process, the to-be-detected object is in a static state, but actual measurement is performed in a moving state. As such, in the embodiments of the disclosure, the compensation of the to-be-detected object during dynamic measurement is taken in to consideration (corresponding to the situation 1 in Table (1)), so that formula (4) is corrected and a compensation value c is added (to form a dynamic correction formula):

$$y=ax+b+c \qquad (5)$$

Figure 17:
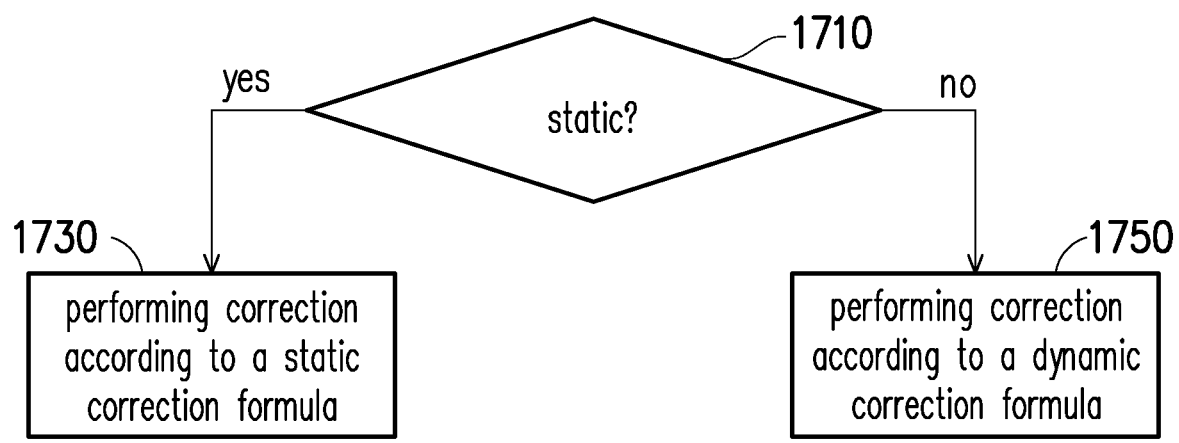
FIG. 17 is a flow chart of correction of a temperature according to an embodiment of the disclosure.

FIG. 17 is a flow chart of correction of a temperature according to an embodiment of the disclosure. With reference to FIG. 1, the processor 130 may determine whether the to-be-detected object is in a static state according to the determination result obtained from Table (1) (step S1710). For instance, situation 1 is a moving state, and situation 3 is a static state. If it is in the static state, the processor 130 may correct a temperature according to the static correction formula (4) (step S1730). If it is in the moving state, the processor 130 may correct the temperature according to the dynamic correction formula (5) (step S1750).

If only the temperature sensor 10 is used to determine the distance, the clothing worn by a person may cover the skin, resulting in an excessive error in distance estimation and measurement. In the embodiments of the disclosure, since accurate distance information is obtained from the position sensing data obtained by the distance sensor 30, the corrected temperature is closer to the actual temperature.

In some embodiments, the processor 130 may combine the thermal image with the aforementioned mapping results (e.g., the position, distance, and/or correction temperature of the to-be-detected object), and rich and accurate information is presented by the display 50.

In view of the foregoing, in the hybrid body temperature measurement system and the method thereof provided by the embodiments of the disclosure, the distance sensing data obtained by the distance sensor may be mapped (or matched) with the thermal image (or array data) to confirm the position, number, and temperature of the to-be-detected object in the thermal image. In this way, the accuracy of position, number, and temperature detection may be improved, and the detection of multiple to-be-detected objects may be accomplished.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A hybrid body temperature measurement method, adapted for execution by a processor included in a computing apparatus, the method comprising:
receiving position sensing data and a thermal image from a distance sensor and a temperature sensor respectively, wherein the distance sensor and the temperature sensor are disposed at a reference position and face a same direction with a same horizontal center, the position sensing data comprises a distance and an azimuth of at least one to-be-detected object relative to the reference position, and the thermal image is formed in response to a temperature of an area in a field of view of the temperature sensor;
dividing the thermal image into a plurality of blocks according to a plurality of vertical lines and mapping the azimuth of the at least one to-be-detected object included in the position sensing data to a corresponding block in the thermal image;
generating a mapping result by mapping the corresponding block in the thermal image to the distance corresponding to the at least one to-be-detected object based on the azimuth of the at least one to-be-detected object; and
determining the at least one to-be-detected object to be a biological body among a plurality of thermal spots detected in the area in the field of view of the thermal image and a position of the at least one to-be-detected object in the thermal image according to the mapping result,
wherein the step of determining the position of the at least one to-be-detected object in the thermal image according to the mapping result comprises:
determining at least one target block from the plurality of blocks, wherein each of the at least one target block comprises the at least one to-be-detected object;
in response to the mapping result indicating one of the at least one target block in the thermal image comprises a plurality of distances included in the position data, and each of the plurality of distances corresponding to one of the at least one to-be-detected object, dividing the one of the at least one target block into a plurality of second sub-blocks according to a number of the distances, wherein an arrangement direction of the second sub-blocks is perpendicular to an arrangement direction of the blocks; and
determining a corresponding second sub-block from among the plurality of second sub-blocks for each of the at least one to-be-detected object present in the one of the at least one target block, according to the distance between the at least one to-be-detected object and the reference position.

2. The hybrid body temperature measurement method according to claim 1, wherein the step of mapping the position sensing data to the thermal image to generate the mapping result further comprises:
determining whether the at least one to-be-detected object is present in each of the blocks to generate a determination result according to the temperature to which the thermal image respond; and
comparing the determination result of the thermal image with the position sensing data to generate the mapping result.

3. The hybrid body temperature measurement method according to claim 2, wherein the step of generating the determination result comprises:
determining a representative temperature of at least one sub-block in each of the blocks; and
determining whether the at least one to-be-detected object is present in the corresponding block according to a comparison result of the representative temperature and a temperature threshold.

4. The hybrid body temperature measurement method according to claim 3, wherein the step of determining the representative temperature of each of the blocks comprises:
determining an average temperature of each of the at least one sub-block; and determining a temperature standard deviation according to the average temperature, wherein the temperature standard deviation acts as the representative temperature.

5. The hybrid body temperature measurement method according to claim 3, wherein the step of generating the determination result comprises:
   determining an average temperature of each of the at least one sub-block, wherein the average temperature acts as the representative temperature.

6. The hybrid body temperature measurement method according to claim 2, wherein the step of comparing the determination result of the thermal image with the position sensing data comprises:
   converting the azimuth corresponding to the at least one to-be-detected object in the position sensing data into a corresponding block in the thermal image;
   determining that the at least one to-be-detected object is present in both the determination result of each of the blocks and the position sensing data on the same block; and
   accordingly generating the mapping result.

7. The hybrid body temperature measurement method according to claim 2, wherein the step of determining the position of the at least one to-be-detected object in the thermal image according to the mapping result further comprises:
   determining at least one sub-block with a highest temperature among a plurality of sub-blocks in each of the at least one target block in the thermal image; and
   determining the position of the at least one to-be-detected object according to the at least one sub-block with the highest temperature.

8. The hybrid body temperature measurement method according to claim 1, further comprising:
   compensating a temperature corresponding to the at least one to-be-detected object in the thermal image according to the position of the at least one to-be-detected object in the thermal image; and
   outputting the thermal image with the position, distance and the compensated temperature of the at least one to-be-detected object to a display.

9. The hybrid body temperature measurement method according to claim 1, wherein the position sensing data is obtained by the distance sensor, the thermal image is obtained by the temperature sensor and is configured for displaying by a display, and both the distance sensor and the temperature sensor are disposed in a vertical direction of the reference position.

10. A hybrid body temperature measurement system, comprising:
    a distance sensor;
    a temperature sensor, wherein the distance sensor and the temperature sensor are disposed at a reference position and face a same direction with a same horizontal center; and
    a computing apparatus, comprising a processor configured for:
    receiving position sensing data and a thermal image from the distance sensor and the temperature sensor respectively, wherein the position sensing data comprises a distance and an azimuth of at least one to-be-detected object relative to the reference position, and the thermal image is formed in response to a temperature of an area in a field of view of the temperature sensor;
    dividing the thermal image into a plurality of blocks according to a plurality of vertical lines and mapping the azimuth of the at least one to-be-detected object included in the position sensing data to a corresponding block in the thermal image;
    generating a mapping result by mapping the corresponding block in the thermal image to the distance corresponding to the at least one to-be-detected object based on the azimuth of the at least one to-be-detected object; and
    determining the at least one to-be-detected object to be a biological body among a plurality of thermal spots detected in the area in the field of view of the thermal image and a position of the at least one to-be-detected object in the thermal image according to the mapping result,
    wherein the processor is further configured for:
    determining at least one target block from the plurality of blocks, wherein each of the at least one target block comprises the at least one to-be-detected object;
    in response to the mapping result indicating one of the at least one target block in the thermal image comprises a plurality of distances included in the position data, and each of the plurality of distances corresponding to one of the at least one to-be-detected object, dividing the one of the at least one target block into a plurality of second sub-blocks according to a number of the distances, wherein an arrangement direction of the second sub-blocks is perpendicular to an arrangement direction of the blocks; and
    determining a corresponding second sub-block from among the plurality of second sub-blocks for each of the at least one to-be-detected object present in the one of the at least one target block, according to the distance between the at least one to-be-detected object and the reference position.

11. The hybrid body temperature measurement system according to claim 10, wherein the processor is further configured for:
    determining whether the at least one to-be-detected object is present in each of the blocks to generate a determination result according to the temperature to which the thermal image respond; and
    comparing the determination result of the thermal image with the position sensing data to generate the mapping result.

12. The hybrid body temperature measurement system according to claim 11, wherein the processor is further configured for:
    determining a representative temperature of at least one sub-block in each of the blocks; and
    determining whether the at least one to-be-detected object is present in the corresponding block according to a comparison result of the representative temperature and a temperature threshold.

13. The hybrid body temperature measurement system according to claim 12, wherein the processor is further configured for:
    determining an average temperature of each of the at least one sub-block; and
    determining a temperature standard deviation according to the average temperature, wherein the temperature standard deviation acts as the representative temperature.

14. The hybrid body temperature measurement system according to claim 12, wherein the processor is further configured for:

determining an average temperature of each of the at least one sub-block, wherein the average temperature acts as the representative temperature.

15. The hybrid body temperature measurement system according to claim 11, wherein the processor is further configured for:
    converting the azimuth corresponding to the at least one to-be-detected object in the position sensing data into a corresponding block in the thermal image; and
    determining that the at least one to-be-detected object is present in both the determination result of each of the blocks and the position sensing data on the same block and accordingly generating the mapping result.

16. The hybrid body temperature measurement system according to claim 11, wherein the processor is further configured for:
    determining at least one sub-block with a highest temperature among a plurality of sub-blocks in each of the at least one target block in the thermal image; and
    determining the position of the at least one to-be-detected object according to the at least one sub-block with the highest temperature.

17. The hybrid body temperature measurement system according to claim 10, further comprising a display and wherein the processor is further configured for:
    compensating a temperature corresponding to the at least one to-be-detected object in the thermal image according to the position of the at least one to-be-detected object in the thermal image; and
    outputting the thermal image with the position, distance and the compensated temperature of the at least one to-be-detected object to the display.

18. The hybrid body temperature measurement system according to claim 10, further comprising:
    the distance sensor, coupled to the processor, configured to obtain the position sensing data; and
    the temperature sensor, coupled to the processor, configured to obtain the thermal image, wherein the thermal image is configured for displaying by a display, and both the distance sensor and the temperature sensor are disposed in a vertical direction of the reference position.

* * * * *